US010760104B2

(12) United States Patent
Noack et al.

(10) Patent No.: US 10,760,104 B2
(45) Date of Patent: Sep. 1, 2020

(54) METHOD OF PRODUCING D-XYLONATE AND CORYNEFORM BACTERIUM (71) Applicant: Forschungszentrum Juelich GmbH, Juelich (DE)

(72) Inventors: Stephan Noack, Wegberg (DE); Andreas Radek, Cologne (DE); Jan Marienhagen, Aachen (DE); Karin Krumbach, Dueren (DE)

(73) Assignee: FORSCHUNGSZENTRUM JUELICH GMBH, Juelich (DE)

( * ) Notice: Subject to any disclaimer, the term of this patent is extended or adjusted under 35 U.S.C. 154(b) by 0 days.

(21) Appl. No.: 16/304,144

(22) PCT Filed: May 19, 2017

(86) PCT No.: PCT/DE2017/000138
§ 371 (c)(1),
(2) Date: Nov. 22, 2018

(87) PCT Pub. No.: WO2017/220059
PCT Pub. Date: Dec. 28, 2017

(65) Prior Publication Data
US 2019/0203236 A1 Jul. 4, 2019

(30) Foreign Application Priority Data
Jun. 25, 2016 (DE) ........................ 10 2016 007 810

(51) Int. Cl.
C12N 1/20 (2006.01)
C12P 7/58 (2006.01)
C07K 14/34 (2006.01)
C12N 1/36 (2006.01)

(52) U.S. Cl.
CPC ............... *C12P 7/58* (2013.01); *C07K 14/34* (2013.01); *C12N 1/36* (2013.01)

(58) Field of Classification Search
CPC ........................................................ C12N 1/20
USPC ....................................................... 435/254.1
See application file for complete search history.

(56) References Cited

U.S. PATENT DOCUMENTS

2012/0005788 A1    1/2012  Richard et al.
2013/0295621 A1*  11/2013  Nishio ...................... C12P 7/50
                                                              435/107

OTHER PUBLICATIONS

Liu et al. Bioresource Technology 115 (2012) 244-248 (Year: 2012).*
Krings, et al. "Characterization of myo-lnositol Utilization by Corynebacterium glutamicum: the Stimulon, Identification of Trans-porters, and Influence on L-Lysine Formation," *Journal of Bacteriology* 188, 23: 8054-8061 (Dec. 2006).
Michael Vogt, et al., "Pushing product formation to its limit: Metabolic engineering of Corynebacterium glutamicum for L-leucine overproduction", Metabolic Engineering, vol. 22, Mar. 2014, pp. 40-52.
Hideo Kawaguchi, et al., "Engineering of a Xylose Metabolic Pathway in Corynebacterium glutamicum", Applied Environmental Microbiology, vol. 72, No. 5, May 2006, pp. 3418-3428.
Andreas Radek, et al., "Engineering of Corynebacterium glutamicum for minimized carbon loss during utilization of D-xylose containing substrates", Journal of Biotechnology, vol. 192, Oct. 7, 2014 (Oct. 7, 2014), pp. 156-160, XP029104817.
S. Klaffl, et al., "Complex Regulation of the Phosphoenolpyruvate Carboxykinase Gene pck and Characterization of Its GntR-Type Regulator IolR as a Repressor of myo-Inositol Utilization Genes in Corynebacterium glutamicum", Journal of Bacteriology, vol. 195, No. 18, Jul. 19, 2013 (Jul. 19, 2013), pp. 4283-4296, XP055409058.
Valeria Tschiginewa, "Regulation der C-Quellenverwertung in *Mycobacterium tuberculosis* and *Mycobacterium bovis* BCG Dissertation", Thesis, Jan. 1, 2015 (Jan. 1, 2015), pp. 1-127, XP055409231.
Mervi H Toivari, et al., "Microbial-xylonate production", Applied Microbiology and Biotechnology, vol. 96, No. 1, Aug. 9, 2012 (Aug. 9, 2012), pp. 1-8, XP035107813.
Martin I. Voskuil, et al., The-16 region of Bacillus subtilis and other gram-positive bacterial promoters, Nucleic Acids Research, vol. 26, No. 15, Feb. 23, 1998, pp. 3584-3590.
Judith Becker, et al., "Bio-based production of chemicals, materials and fuels—Corynebacterium glutamicum as versatile cell factory", Current Opinion in Biotechnology, vol. 23, Dec. 2, 2011, pp. 631-640.
Jessica Boyd, et al., "Analysis of the Diphtheria tox Promoter by Site-Directed Mutagenesis", Journal of Bacteriology, vol. 170, No. 12, Dec. 1988, pp. 5949-5952.
Johanna Buchert, et al., "The role of vylonolactone in xylonic acid production by Pseudomonas fragi", Applied Microbiology Biotechnology, vol. 27, Dec. 1988, pp. 333-336.
Nikolay V. Dokholyan, "What Is the Protein Design Alphabet?", Proteins: Structure, Function, and Bioinformation, vol. 54, Dec. 2004, pp. 622-628.
Horace S. Isbell, "Oxidation of Aldoses With Bromine", Journal of Research of the National Bureau of Standards-A. Physics and Chemistry, vol. 66A, No. 3, May-Jun. 1962, pp. 327-338.
Rainer Jaenicke, et al., "Protein Design at the Crossroads of Biotechnology, Chemistry, Theory, and Evolution", Angew. Chem. Int. Ed., vol. 42, No. 2, Dec. 2003, pp. 140-142.
Peter Ruhdal Jensen, et al., "Artificial Promoters for Metabolic Optimization", Biotechnology Bioengineering, vol. 58, Nos. 2, 3, Apr. 20-May 5, 1998, pp. 191-195.
A.: Jokic, et al., "Simultaneous electrolytic production of xlitol and xylonic acid from xylose", Journal of Applied Electrochemistry, vol. 21, Dec. 1991, pp. 321-326.
Hauke Lilie, "Designer proteins in biotechnology", EMBO reports, vol. 4, No. 4, Mar. 14, 2003, pp. 1-6.

(Continued)

*Primary Examiner* — Tekchand Saidha
(74) *Attorney, Agent, or Firm* — Leydig, Voit & Mayer, Ltd.

(57) ABSTRACT

The invention relates to a method of producing D-xylonate from D-xylose, which includes converting D-xylose to D-xylonate from a coryneform bacterium in which the activity of the iolR gene is reduced or completely switched off compared with the wild type or a mutation of the wild type, or the iolR gene is completed or partially deleted, as well as to a bacterium for carrying out the method.

20 Claims, 2 Drawing Sheets

Specification includes a Sequence Listing.

(56) References Cited

OTHER PUBLICATIONS

Huaiwei Liu, et al., "High yield production of C-Xylonic acid from C-xylose using engineered *Escherichia coli*", Biosource Technology, vol. 115, Dec. 2012, pp. 244-248.

Nicole Paczia, et al., "Extensive exometabolome analysis reveals extended overflow metabolism in various microorganisms", Microbial Cell Factories, vol. 11, Dec. 2012, pp. 1-14.

Miroslav Pátek, et al., "Promoters from Corynebacterium glutamicum: cloning, molecular analysis and search for a consensus motif", Microbiology, vol. 142, Dec. 1996, pp. 1297-1309.

Jimin Pei, et al., "Using protein design for homology detection and active site searches", PNAS, vol. 100, No. 20, Sep. 30, 2003, pp. 11361-11366.

F. Pezzotti, et al., "Enzymatic synthesis of aldonic acids", Carbohydrate Research, vol. 341, Jun. 27, 2006, pp. 2290-2292.

Navin Pokala, et al., "Review: Protein Design-Where, We were, Where we are, Where we're going", Journal of Structural Biology, vol. 134, Dec. 2001, pp. 269-281.

Mervi Toivari, et al., "Metabolic engineering of *Saccharomyces cerevisiae* for bioconversion of D-xylose to D-xylonate", Metabolic Engineering, vol. 14, Dec. 2012, pp. 427-436.

Anna Tramontano, "A Brighter Future for Protein Design", Angew. Chem. Int. Ed., vol. 43, Dec. 2004, pp. 3222-3223.

Simon Unthan, et al., "Beyond Growth Rate 0.6: What Drives Corynebacterium glutamicum to Higher Growth Rates in Defined Medium", Biotechnology and Bioengineering, vol. 111, No. 2, Feb. 2014, pp. 1-13.

\* cited by examiner

SEQUENCE LISTING

<160> NUMBER OF SEQ ID NOS: 2

<210> SEQ ID NO 1
<211> LENGTH: 759
<212> TYPE: DNA
<213> ORGANISM: Corynebacterium glutamicum

<400> SEQUENCE: 1

```
atgaccaccg aagctcccat ttggccagcc gaactcttcg aagacctcga ccgcaacgga      60
ccaatccccc tctacttcca agtagcccaa cgcctcgaag acggcatccg cagcggagtc     120
ctcccacccg gagcacgcct agaaaacgag atctccgtgg cgaaacacct caacgtatcc     180
cgccccaccg tccgacgcgc catccaagaa gtcgtagaca aaggcctctt agttcgccgc     240
cgcggtgttg gcacccaggt cgtccaaagc cacgtcaccc gcccagtcga actgaccagt     300
ttcttcaacg acctcaaaaa cgccaacctg gaccccaaaa cccgagtcct cgagcaccgc     360
ctccttgcag caagttccgc catcgcagaa aaactcggag tttccgcagg tgacgaagtc     420
ctcctcatcc gccgcctccg ctccaccgga gacatccccg tagcgatcct ggaaaactac     480
ctccccccag cgttcaacga cgtctccctc gacgaactag aaaagggtgg actctacgat     540
gcgctgcgca gccgaggtgt tgtcttaaaa atcgccaacc agaaaatcgg tgcgcgccga     600
gcagtcggtg aagaaagcac cctcctcgac atcgaagacg gcggaccact tctcaccgtc     660
```

-continued

```
gaacgcgttg cattggataa ttccggccaa gtaatcgagt tgggaagcca ctgctaccgc    720
ccagatatgt acaactttga aaccactctg gtggccagg                          759

<210> SEQ ID NO 2
<211> LENGTH: 1259
<212> TYPE: DNA
<213> ORGANISM: Corynebacterium glutamicum

<400> SEQUENCE: 2
ccctcgcttt ggaaggtgcg gggttaacaa agttgcacgt tatgacctgc aaactctgcc     60
cttttcacta agtttcgcta ctcattccct aatgcaagtg ataatgtcag atcaataaaa    120
gccctggatg acacaaaagt cctgcatgaa cacggattta ccaagaccac cacccgcaac    180
tcagttacat tgttcaaatg tcctaacaca tttacatgag cttgttgggt gggcaacgaa    240
aggagacatc atgaccaccg aagctcccat ttggccagcc gaactcttcg aagacctcga    300
ccgcaacgga ccaatccccc tctacttcca agtagcccaa cgcctcgaag acggcatccg    360
cagcggagtc ctcccacccg gagcacgcct agaaaacgag atctccgtgg cgaaacacct    420
caacgtatcc cgccccaccg tccgacgcgc catccaagaa gtcgtagaca aaggcctctt    480
agttcgccgc cgcggtgttg gcacccaggt cgtccaaagc cacgtcaccc gccagtcga    540 actgaccagt ttcttcaacg acctcaaaaa cgccaacctg daccccaaaa cccgagtcct    600
cgagcaccgc ctccttgcag caagttccgc catcgcagaa aaactcggag tttccgcagg    660
tgacgaagtc ctcctcatcc gccgcctccg ctccaccgga gacatccccg tagcgatcct    720
ggaaaactac ctccccccag cgttcaacga cgtctccctc gacgaactag aaaagggtgg    780
actctacgat gcgctgcgca gccgaggtgt tgtcttaaaa atcgccaacc agaaaatcgg    840
tgcgcgccga gcagtcggtg aagaaagcac cctcctcgac atcgaagacg gcggaccact    900
tctcaccgtc gaacgcgttg cattggataa ttccggccaa gtaatcgagt tgggaagcca    960
ctgctaccgc ccagatatgt acaactttga aaccactctg gtggccaggt aagaaataaa   1020
ccaaagagcc cttctgaact ggagctcttg gtctgatatg gcattttcaa ggctggaaaa   1080
ctgctctatc agaccaaacg gatgctgaat ttcagggtct ttggtctgga tatgcagcag   1140
cgctccaagg cgtcgagttt ctcaaacgag cattggtatc gatgacaccc tgaaaggccc   1200
ttagaagcga ttctgtgagg tcgagttccc agggtttgag tgcaagtttt ttacgtgaa    1259
```

METHOD OF PRODUCING D-XYLONATE AND CORYNEFORM BACTERIUM

CROSS-REFERENCE TO PRIOR APPLICATIONS

This application is a U.S. National Phase application under 35 U.S.C. § 371 of International Application No. PCT/DE2017/000138, filed on May 19, 2017, and claims benefit to German Patent Application No. DE 10 2016 007 810.3, filed on Jun. 25, 2016. The International Application was published in German on Dec. 28, 2017 as WO 2017/220059 A1 under PCT Article 21(2).

INCORPORATION BY REFERENCE OF ELECTRONICALLY SUBMITTED MATERIALS

Incorporated by reference in its entirety herein is a computer-readable nucleotide/amino acid sequence listing submitted herewith and identified as follows: 3,133 bytes ASCII (Text) file named "816712_ST25," created Nov. 15, 2018.

FIELD

The invention relates to a method for producing D-xylonate and to a coryneform bacterium.

BACKGROUND

D-Xylonic acid ($C_5H_{10}O_6$) is an organic acid that, as set out by Toivari et al. in Appl Microbiol Biotechnol, 2012, 96(1): 1-8, can be used as a precursor for polyamides, polyesters and 1,2,4-butanetriol and thus has high potential for use in the pharmaceutical industry, the food industry and the chemical industry. The following explanations relate to D-xylonate, the salt of D-xylonic acid. D-Xylonate is in the top 30 high-potential precursor chemicals based on $2^{nd}$ generation renewable raw materials, e.g. pentose-containing hemicelluloses. D-Xylonate is similar to D-gluconate ($C_6H_{11}O_7$), which has a global market of 80 kt/year.

D-Xylonate is naturally formed in some bacteria in a two-stage reaction. In the first reaction, D-xylose is oxidized to form D-xylonolactone, specific dehydrogenases being catalytically active here depending on the organism. The D-xylonolactone can then be converted to D-xylonate either by specific lactonases or spontaneously, without an enzyme catalyst. For example, for the species *Gluconobacter oxydans* and *Pseudomonas fragi*, high product titers of D-xylonate have been reported (Buchert et al., Applied Microbiology and Biotechnology, 27(4): 333-336, Toivari et al., Appl Microbiol Biotechnol, 2012, 96(1): 1-8).

Furthermore, alternative D-xylonate production strains (e.g. yeast of the species *Saccharomyces cerevisiae*, bacteria of the species *Escherichia coli* and fungi of the species *Aspergillus niger*) are produced by heterologous expression of D-xylose dehydrogenases, e.g. from *Caulobacter crescentus*, as set out in (Liu et al., BioresourTechnol, 2012, 115: 244-248, Richard et al., 2012, US20120005788 A1 (U.S. Ser. No. 13/256,559), Toivari et al., Metab Eng, 2012, 14(4): 427-436).

In addition to microbial production, D-xylonate can be produced electrochemically (Jokic et al., Journal of Applied Electrochemistry, 21(4): 321-326), enzymatically (Pezzotti et al., Carbohydr Res, 2006, 341(13): 2290-2292) or by chemical oxidation (Isbell et al., Bureau of Standards Journal of Research, 1932, 8(3): 327-338).

It is known that organic acids or the salts thereof can be produced by fermentation of strains of coryneform bacteria, in particular *Corynebacterium glutamicum*.

US 2013/0295621 A1 discloses a method for producing D-xylonic acid using genetically modified bacteria.

The production strains known from the prior art that have endogenic D-xylonate synthesis capacity, such as *Gluconobacter oxydans*, require undefined media for growth, meaning that D-xylonate production becomes significantly more complex, expensive and thus uneconomical.

All the previously described "unnatural" D-xylonate producers are genetically modified organisms within the meaning of the German Genetic Engineering Act (GenTG), Section 3, according to which an organism is genetically modified when it is capable of heterologous expression or it contains genes foreign to this organism, i.e. is recombinantly modified, inter alia various yeasts, fungi and bacteria. This is a drawback for use in certain industrial sectors, such as the food and pharmaceutical industries, due to complex approval procedures.

There is a need to provide a method and a microorganism using which D-xylonate and therefore D-xylonic acid can be produced at high enantiomeric purity and with a high yield. In particular, a microorganism and a method are provided which can be used in industrial applications, in particular in the food industry, the pharmaceutical industry and the chemical industry and readily meet the approval conditions for use in the food industry as well as in the pharmaceutical and chemical industries. The drawbacks associated with genetically modified organisms within the meaning of the German Genetic Engineering Act, Section 3, in particular the drawbacks associated with recombinantly modified organisms, are preferably intended to be avoided. In particular, it is desirable to use simple and cost-effective culture media that are inexpensive and easy to use. The microorganisms used are intended to have high growth rates on defined media, to achieve high biomass yields and to simplify the subsequent product processing.

SUMMARY

In an embodiment, the present invention provides a method for microbial production of D-xylonate from D-xylose, comprising converting D-xylose to D-xylonate from a coryneform bacterium in which the activity of the iolR gene is reduced or completely switched off compared with the wild type or a mutation of the wild type or the iolR gene is completed or partially deleted.

In another embodiment, the present invention provides a coryneform bacterium, wherein the activity of the iolR gene is reduced or completely switched off compared with the wild type or a mutation of the wild type or the iolR gene is completed or partially deleted.

Figure 1:
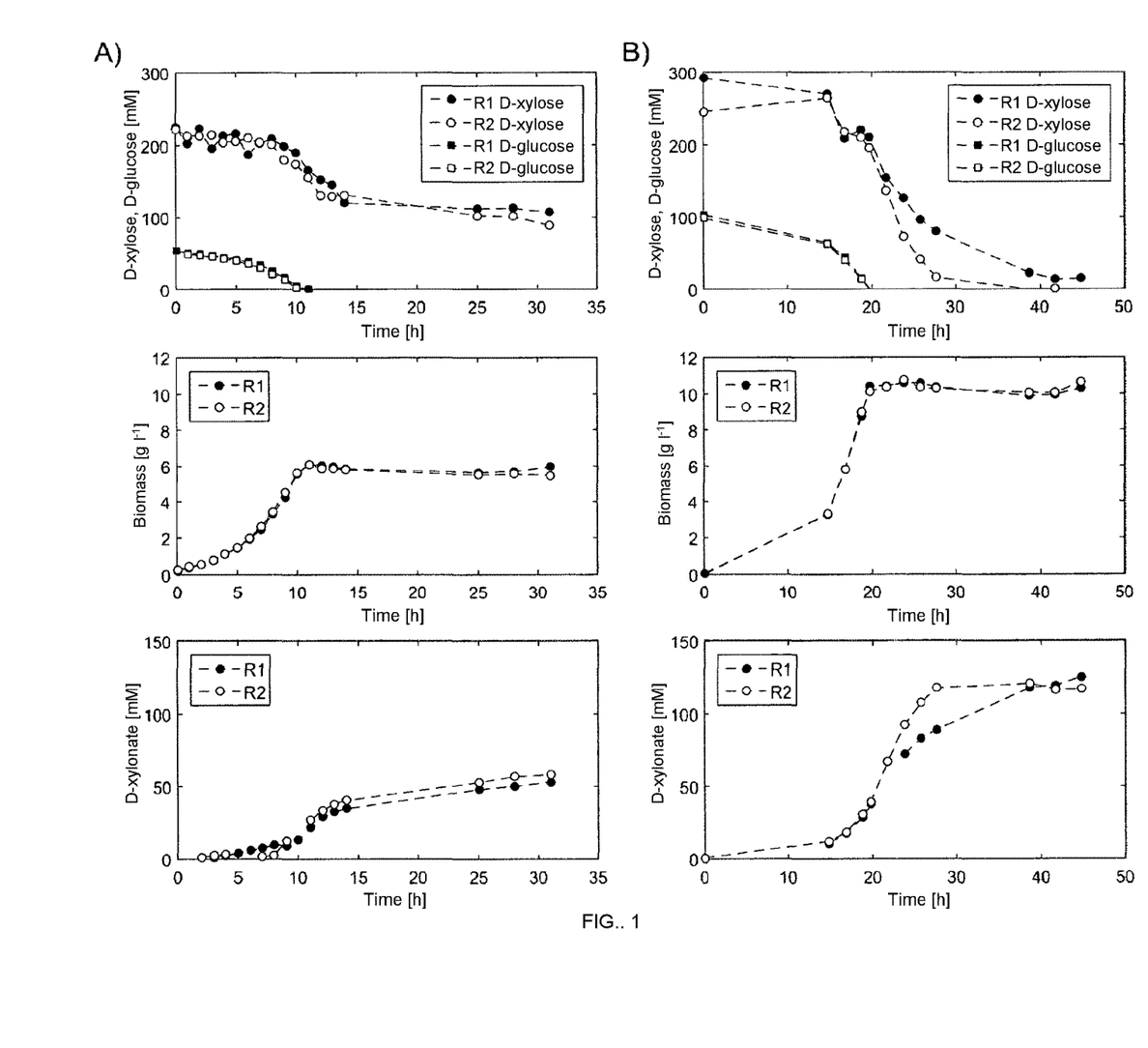
FIG. 1 shows cultivation curves for the strain *Corynebacterium glutamicum* ΔiolR.

FIG. 1 shows cultivation curves for the strain *Corynebacterium glutamicum* ΔiolR in the sub-figures A) and B). Here, the x axes of the graphs in all the sub-figures are time in hours h. They axes of the first row are the quantity of D-xylose and D-glucose in millimoles [mM].

They axes of the second row are the biomass in grams per liter [g/l] and they axes of the third row are the quantity of D-xylonate in millimoles [mM].

Sub-FIG. 1A shows the cultivation curves for the strain *C. glutamicum* ΔiolR in the batch process. A final titer of D-xylonate of 9.2±0.6 g/l was achieved. The specific yield and production rate are $Y_{P/S}$=0.49±0.01 g D-xylonate/g D-xylose and 30±0.02 g/(l h). Sub-FIG. 1B shows the cultivation curves for the strain *C. glutamicum* ΔiolR in the fed batch process. A final titer of D-xylonate of 20.0±1.0 g/l was achieved. The specific yield and production rate are $Y_{P/S}$=0.51±0.02 g D-xylonate/g D-xylose and 0.45±0.02 g/(l h).

Figure 2:
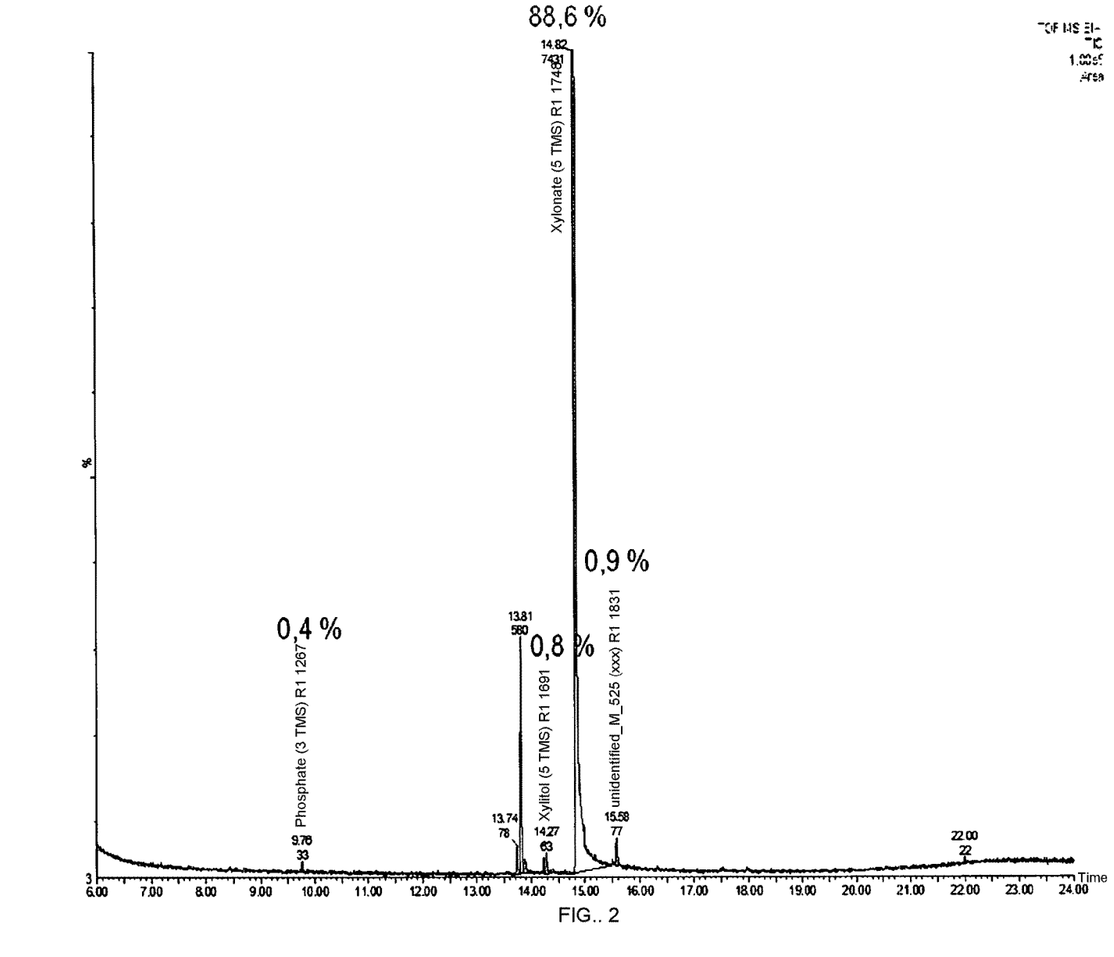
FIG. 2 shows a GC-ToF-MS spectrum for a purified precipitate.

FIG. 2 shows the spectrum of the purified precipitate, which was produced by means of GC-ToF-MS analysis (Paczia et al., Microbial Cell Factories, 2012, 11). In this figure, the y axis is the relative peak intensity and is plotted against the chromatographic time of flight on the x axis.

DETAILED DESCRIPTION

Using the microorganism according to embodiments of the invention, its genome and the production method according to embodiments of the invention, it is now possible to produce D-xylonate with a high yield, for example >0.5 g D-xylonate/g D-xylose, at an enantiomeric purity of 100%. The microorganisms according to embodiments of the invention are well suited to industrial use and, in a preferred embodiment, meet the approval criteria for use in the food industry and in the pharmaceutical and chemical industries, and in particular they are considered not to be recombinantly modified in accordance with the German Genetic Engineering Act. The microorganisms according to embodiments of the invention achieve high growth rates and high biomass yields on defined media, and allow for simple product processing. Drawbacks from the prior art have been overcome. The defined media are less expensive and less complex to use. The growth of the production organisms is more reproducible than in undefined media. The complexity of the media is low, and this therefore reduces the number of method steps required for product processing.

In the following, the invention is described in general terms, without this being considered limiting.

It has surprisingly been found that a very high yield of enantiomerically pure D-xylonate can be achieved using coryneform bacteria in which the activity of the iolR gene, coding for a regulator of the myo-inositol metabolism, referred to in the following as the iolR gene, is reduced or switched off or in which the iolR gene is at least partially deleted, proceeding from D-xylonate as the substrate.

The invention therefore relates to a coryneform bacterium in which the activity of the iolR gene is reduced or completely switched off compared with the wild type or a mutation of the wild type, preferably a non-recombinant mutation that contains this gene, or in which the iolR gene is at least partially deleted, and to a method for producing D-xylonate using a coryneform bacterium in which the activity of the iolR gene is reduced or completely switched off or in which the iolR gene is at least partially deleted.

The coryneform bacteria modified according to certain embodiments of the invention may originate from the wild type or from a form that has been genetically modified from the wild type and has preferably not been recombinantly modified.

The strains that originate from the wild type are particularly preferred for the pharmaceutical and food industries since they are approved for production particularly easily.

The wild type contains a natural iolR gene as the parent strain in the method according to certain embodiments of the invention.

The genetically modified strains likewise contain a natural iolR gene in the parent strain thereof. Within the meaning of the invention, a genetically modified strain is for example understood to be strain that is genetically modified such that targets or target genes of the regulator iolR are hyperexpressed. All or some of the genes that are relevant to myo-inositol metabolism and code for the enzymes for the myo-inositol metabolism can be over-expressed. For this purpose, genes that code for these enzymes and allow increased expression of these genes can for example be integrated into the genome. The genes can also be introduced chromosomally. Other activation mechanisms for the increased expression of enzymes for the myo-inositol metabolism are also conceivable, for example the introduction of stronger promoters and the modulation of the translation efficiency. Furthermore, the stability of enzymes for the myo-inositol metabolism can also be increased.

In particular, coryneform bacteria of the species *Corynebacterium, Brevibacterium*, in particular *Corynebacterium glutamicum, Corynebacterium acetoglutamicum, Corynebacterium thermoaminogenes, Brevibacterium flavum, Brevibacterium lactofermentum* or *Brevibacterium divaricatum* can be used.

Coryneform bacteria that are modified according to the invention proceeding from the wild type are preferred; for example the wild types

*Corynebacterium glutamicum* ATCC13032
*Corynebacterium acetoglutamicum* ATCC15806
*Corynebacterium acetoacidophilum* ATCC13870
*Corynebacterium thermoaminogenes* FERM BP-1539
*Brevibacterium flavum* ATCC14067
*Brevibacterium lactofermentum* ATCC13869 and
*Brevibacterium divaricatum* ATCC14020 are used. This list is not limiting, but given by way of example.

The use of *Corynebacterium glutamicum* as a production organism provides particular advantages since
i) it is a "generally recognized as safe" (GRAS) organism which can be used in all industrial sectors;
ii) high growth rates and biomass yields are thus achieved on defined media (Unthan et al., Biotechnol Bioeng, 2014, 111(2): 359-371) and
iii) there is extensive experience in industrial use (Becker et al., Curr Opin Biotechnol, 2012, 23(4): 631-640).

The partial inactivation, inactivation or the partial deletion or complete deletion of the myo-inositol metabolism regulator iolR, in particular iolR (cg0196) in coryneform bacteria, preferably *Corynebacterium glutamicum* ATCC13032, causes the formation of D-xylonate from D-xylose. This preferred embodiment has the advantage that, as the wild type modified according to the invention, it is not subject to any approval restrictions in chemical, pharmaceutical or food production.

In the preferred embodiment, the iolR gene is completely switched off.

This may preferably be carried out by completely deleting the iolR gene. Provided that the inactivation of the iolR gene is complete, this can also be caused by partial deletion.

The iolR gene can also be completely inactivated by other measures known to a person skilled in the art. For example, suitable cultivation, e.g. by using myo-inositol as a substrate/inductor of iolR, can be referred to as inserting another DNA sequence into the gene segment of the iolR gene, in particular the iolR gene cg0196. Within the meaning of the invention, a gene segment is understood to be a segment in which the modification still has an effect on the activity of the iolR gene. This segment can be located before, after or in the open reading frame of the iolR gene.

Complete inactivation can also take place by completely switching off the gene expression of iolR by genetically modifying (mutating) the signal structures of the gene expression. Signal structures of the gene expression are for example repressor genes, activator genes, operators, promoters, attenuators, ribosome bonding points, the start codon and terminators. A person skilled in the art can find information on this e.g. in the patent application WO 96/15246, in Boyd and Murphy (Boyd et al., J Bacteriol, 1988, 170(12): 5949-5952), in Voskuil and Chambliss (Voskuil et al., Nucleic Acids Research, 1998, 26(15): 3584-3590), in Jensen and Hammer (Jensen et al., Biotechnol Bioeng, 1998, 58(2-3): 191-195), in Patek et al. (Patek et al., Microbiology, 1996, 142 (Pt 5): 1297-1309), and in known textbooks on genetics and microbiology, such as the textbook by Knippers ("Molekulare Genetik" [Molecular Genetics], 8th edition, Georg Thieme Verlag, Stuttgart, Germany, 2001) or the textbook by Winnacker ("Gene and Klone" [Genes and Clones], VCH Verlagsgesellschaft, Weinheim, Germany, 1990).

Mutations that lead to a modification to the functional properties of iolR, in particular to a modified substrate specificity, could likewise lead to the activity of the iolR gene being completely switched off. Transitions, transversions, insertions and deletions, and methods for directed evolution, come into consideration as mutations. Instructions on producing mutations and proteins of this type are part of the prior art and can be found in known textbooks (R. Knippers "Molekulare Genetik" [Molecular Genetics], 8th edition, 2001, Georg Thieme Verlag, Stuttgart, Germany), or review articles (Pokala et al., J Struct Biol, 2001, 134(2-3): 269-281, Jaenicke et al., Angew Chem Int Ed Engl, 2003, 42(2): 140-142, Lilie, EMBO Rep, 2003, 4(4): 346-351, Pei et al., Proc Natl Acad Sci USA, 2003, 100(20): 11361-11366, Dokholyan, Proteins, 2004, 54(4): 622-628, Tramontano, Angew Chem Int Ed Engl, 2004, 43(25): 3222-3223).

The coryneform bacteria produced in this way have no iolR gene activity whatsoever and lead to production of a high yield of enantiomerically pure D-xylonate. Complete deletion is preferred.

In *Corynebacterium glutamicum* ATCC13032 ΔiolR, the iolR gene cg0196 is completely deleted.

In another embodiment, the activity of the iolR gene is reduced. This can also be caused by partial deletion, provided that the activity has not been completed switched off thereby.

The iolR gene can also be partially inactivated by other measures known to a person skilled in the art. For example, suitable cultivation, e.g. by using myo-inositol as a substrate/inductor of iolR, can be referred to as inserting another DNA sequence into the gene segment of the iolR gene, in particular the iolR gene cg0196. Within the meaning of the invention, a gene segment is understood to be a segment in which the modification still has an effect on the activity of the iolR gene. This segment can be located before, after or in the open reading frame of the iolR gene.

Partial inactivation can also take place by partially switching off the gene expression of iolR by genetically modifying (mutating) the signal structures of the gene expression. Signal structures of the gene expression are for example repressor genes, activator genes, operators, promoters, attenuators, ribosome bonding points, the start codon and terminators. Here, the same methods can in principle be used as those used for complete deletion.

Mutations that lead to a modification to the functional properties of iolR, in particular to a modified substrate specificity, could likewise lead to the activity of the iolR gene being partially switched off. Transitions, transversions, insertions and deletions, and methods for directed evolution, come into consideration as mutations. Here too, the above-mentioned methods can be used.

The above-mentioned genetic modifications according to certain embodiments of the invention result in the coryneform bacteria according to other embodiments of the invention and, with isolation, to the genome according to still other embodiments of the invention.

The iolR gene cg0196 is set out in sequence listing no. 1.

An iolR gene of a coryneform bacterium ATCC13032 having an open reading frame is set out in sequence no. 2.

Surprisingly, the inactivation of the iolR gene on a defined medium together with a carbon and energy source for growth, e.g. D-glucose, and D-xylose as an additional carbon and energy source, causes the formation of D-xylonate. This of course cannot be metabolized by coryneform bacteria, and therefore accumulates in the medium and can then be purified therefrom.

The organisms of coryneform bacteria modified according to certain embodiments of the invention produce a high yield of 100% enantiomerically pure D-xylonate or D-xylonic acid. The genome according to other embodiments of the invention produced in this way allows coryneform bacteria to produce D-xylonate or D-xylonic acid with a high yield and enantiomeric purity of 100%.

The production of the D-xylonate using the coryneform bacteria according to certain embodiments of the invention can be carried out using known fermentation-based methods that are standard in laboratories and in production.

The microorganisms produced according to certain embodiments of the invention can be cultured continuously or discontinuously in a batch process (batch cultivation), in a fed batch process or in a repeated fed batch process for the purpose of D-xylonate production. A summary of known cultivation methods is described in the textbook by Chmiel (Bioprozesstechnik 1. Einfuhrung in die Bioverfahrenstechnik [Bioprocess technology 1: Introduction to bioprocess engineering] (Gustav Fischer Verlag, Stuttgart, 1991)) or in the textbook by Storhas (Bioreaktoren and periphere Einrichtungen [Bioreactors and peripheral equipment] (Vieweg Verlag, Braunschweig/Wiesbaden, 1994)).

The culture medium to be used has to meet the demands of the respective microorganisms in a suitable manner. Descriptions of culture media of different microorganisms are found in the handbook "Manual of Methods for General Bacteriology" by the American Society for Bacteriology (Washington D.C., USA, 1981).

In addition to D-xylose as an initial substrate for D-xylonate formation, sugars and carbohydrates such as glucose, saccharose, lactose, fructose, maltose, molasses, starch and cellulose, oils and fats such as soya oil, sunflower oil, peanut oil and coconut oil, fatty acids such as palmitic acid, stearic acid and linoleic acid, alcohols such as glycerol and ethanol and organic acids such as acetic acid can be used as a carbon source for growth. These substances can be used individually or as a mixture. The CGXII medium (Unthan et al., Biotechnol Bioeng, 2014, 111(2): 359-371) with D-xylose and D-glucose as carbon and energy sources is particularly preferred. As a result, high specific growth rates for *Corynebacterium glutamicum* ATCC13032 of up to 0.61 $h^{-1}$ can be achieved. Furthermore, the use of the CGXII medium ensures that the target product, D-xylonate, is separated from the culture supernatant in a simple manner, e.g. by ethanol precipitation with subsequent vacuum drying (Liu et al., Bioresource Technology, 2012, 115: 244-248). The simple medium is part of the problem to be solved.

Organic, nitrogen-containing compounds such as peptones, yeast extract, meat extract, malt extract, maize steeping liquor, soybean flour and urea or inorganic compounds such as ammonium sulfate, ammonium chloride, ammonium phosphate, ammonium carbonate and ammonium nitrate can be used as the nitrogen source. The nitrogen sources can be used individually or as a mixture.

Potassium dihydrogen phosphate or dipotassium hydrogen phosphate or the corresponding sodium-containing salts can be used as the phosphorus source.

In addition, the culture medium is intended to contain salts of metals such as magnesium sulfate or iron sulfate, which are necessary for growth.

Lastly, essential growth substances, such as amino acids and vitamins, can be used in addition to the above-mentioned substances.

The above-mentioned feedstock can be added to the culture in the form of a single batch or can be fed in during cultivation in a suitable manner.

For the pH control of the culture, basic compounds such as sodium hydroxide, potassium hydroxide, ammonia or acidic compounds such as hydrochloric acid, phosphoric acid or sulfuric acid can be used in a suitable manner. A preferred pH range for cell growth is between 6 and 8.

Anti-foaming agents such as fatty acid polyglycol esters can be used to control foam development.

Oxygen or oxygen-containing gas mixtures such as air are preferably introduced into the culture in order to maintain aerobic conditions.

The temperature of the culture is normally 20° C. to 45° C. and preferably 25° C. to 40° C.

The culturing is preferably continued until a maximum quantity of D-xylonate has formed. This target is usually reached within 10 to 160 hours.

The drawings show experimental results from the examples, which demonstrate the advantages according to the invention.

EXAMPLES

In the following, experimental data is given as examples, which should not be considered limiting.

In order to generate the strain C. glutamicum ΔiolR, the iolR gene was deleted in the reading frame ("in frame") in order not to impair the expression of downstream genes as far as possible. For this purpose, cross-over PCR was carried out. In two first PCRs, two 400-bp-long, upstream and downstream, flanking DNA segments of the gene to be deleted were separately amplified. The oligonucleotides used (iolR_DF1_for CCCAAGCTTGAGGTACTTGC-CGAAAGATTG (HindIII), i-oIR_DF1_rev CTCGAT-TACTTGGCCGGAGGGCTACTTGGAAGTAGAGG, iolR_DF2_for TCCGGCCAAGTAATCGAG, iolR_DF2_rev CGGGATCCATCGCGTTGGCATTCTTC (Bam-HI)) were modified such that the resulting PCR fragments at the 5' end were each connected to an 18-nucleotide-long homologous sequence of which the fragments were complementary to one another. For the cross-over PCR, the products of the first PCRs were used as DNA matrices, addition taking place over the complementary region during the reaction. By using the outer primers, the deletion construct that was cloned in the vector pK19mobsacB was thus produced. Following transformation of this vector, which is not freely replicable, into C. glutamicum and subsequent selection for the kanamycin resistance imparted by pK19mobsacB-ΔiolR2, clones were isolated in which the plasmid was integrated into the chromosome by homologous recombination. By cultivating these cells in a complete medium without kanamycin, it was possible for a second recombination event to take place over the DNA segments that were then duplicated in the chromosome. The bacterial culture was plated on an LB medium with 10% saccharose in different dilutions. Saccharose was polymerized to form levane due to the levane-sucrase coded by sacB on pK19mobsacB-ΔiolR2. This polymer then resulted in lethality. Therefore, it was only possible to grow those clones which had lost the plasmid due to the second recombination. In the then saccharose-resistant and kanamycin-sensitive clones, either the genetic wild type was produced again or the desired gene was deleted. The deletion in the genome of C. glutamicum was confirmed by means of the PCR using primers which were complementary to a segment outside the gene (K_DiolR_for GCACGTTAT GACCTGCAAACTC, K_DiolR_rev TACGGTCTGGCTAT CTACATCC).

The strain C. glutamicum ΔiolR produced in this way was cultivated in the batch process and fed batch process in 1.5 l bioreactors (DASGIP AG, Jülich, Germany) at 30° C. and a constant aeration rate of 1 vvm. Consistently aerobic conditions (>30% dissolved oxygen) were achieved by the oxygen input and by adjusting the stirrer speed (400-1200 rpm). The pH in the cultivation medium was continuously regulated to pH 7.1 using 5 M $H_3PO_4$ and 5 M $NH_4OH$. The batch process was inoculated in two separate reactors from an overnight preculture on the CGXII medium (Unthan et al., Biotechnol Bioeng, 2014, 111(2): 359-371) with 40 g/l D-glucose to an OD of 1 in the CGXII medium without urea and with 10 g/l D-glucose as well as 30 g/l D-xylose. The fed batch process was inoculated in two separate reactors from an overnight preculture on the CGXII medium with 40 g/l D-glucose to an OD of 1 in the CGXII medium without urea and with 20 g/l D-glucose as well as 40 g/l D-xylose. After a processing time of 20 hours with the use of glucose limitation, a continuous feed of 100 g/l D-glucose and a rate of 2.5 ml/h (reactor 1) and Smith (reactor 2) was started. All the cultivations were sampled at regular intervals, the samples were centrifuged and the resulting cell-free supernatant was used for the substrate and product analysis. For the substrate analysis (D-glucose and D-xylose), two enzymatic assays were used (Unthan et al., Microb Cell Fact, 2015, 14: 32) and the product (D-xylonate) was quantified using a DAD detector (Agilent, Santa Clara, Calif., USA) by means of HPLC (300×8 mm organic acid column, CS Chromatographie, Langerwehe, Germany) at 80° C. and an isocratic elution having 0.1 M $H_2SO_4$ and a flow rate of 0.6 ml/min.

At the end of the fed batch cultivation, a reactor was completely harvested for product purification and analysis. For the product purification, an existing protocol (Liu et al., Bioresource Technology, 2012, 115: 244-248) was used as follows: 1. cell separation by means of centrifugation (4500 rpm for 10 min at 4° C.); 2. decolorization of the resulting supernatant in activated carbon (AC); 3. filtration of the AC-treated supernatant (0.22 μm) and concentration by means of a rotary evaporator (100 mbar, 60° C. water bath); 4. filtration of the concentrate (0.22 μm) and precipitation of D-xylonate by adding EtOH (3:1, v/v); vacuum drying of the product for at least 12 hours at −10° C.

Gene sequence of iolR with open reading frame (bold) and 250 bp up and downstream.

CCCTCGCTTTGGAAGGTGCGGGGTTAACAAAGTTGCACGTTATGACCTGC

AAACTCTGCCCTTTTCACTAAGTTTCGCTACTCATTCCCTAATGCAAGTG

ATAATGTCAGATCAATAAAAGCCCTGGATGACACAAAAGTCCTGCATGAA

CACGGATTTACCAAGACCACCACCCGCAACTCAGTTACATTGTTCAAATG

TCCTAACACATTTACATGAGCTTGTTGGGTGGGCAACGAAAGGAGACATC

ATGACCACCGAAGCTCCCATTTGGCCAGCCGAACTCTTCGAAGACCTCGA

CCGCAACGGACCAATCCCCCTCTACTTCCAAGTAGCCCAACGCCTCGAAG

ACGGCATCCGCAGCGGAGTCCTCCCACCCGGAGCACGCCTAGAAAACGAG

ATCTCCGTGGCGAAACACCTCAACGTATCCCGCCCCACCGTCCGACGCGC

CATCCAAGAAGTCGTAGACAAAGGCCTCTTAGTTCGCCGCCGCGGTGTTG

GCACCCAGGTCGTCCAAAGCCACGTCACCCGCCCAGTCGAACTGACCAGT

TTCTTCAACGACCTCAAAAACGCCAACCTGGACCCCAAAACCCGAGTCCT

CGAGCACCGCCTCCTTGCAGCAAGTTCCGCCATCGCAGAAAAACTCGGAG

TTTCCGCAGGTGACGAAGTCCTCCTCATCCGCCGCCTCCGCTCCACCGGA

GACATCCCCGTAGCGATCCTGGAAAACTACCTCCCCCCAGCGTTCAACGA

CGTCTCCCTCGACGAACTAGAAAAGGGTGGACTCTACGATGCGCTGCGCA

GCCGAGGTGTTGTCTTAAAAATCGCCAACCAGAAAATCGGTGCGCGCCGA

GCAGTCGGTGAAGAAAGCACCCTCCTCGACATCGAAGACGGCGGACCACT

TCTCACCGTCGAACGCGTTGCATTGGATAATTCCGGCCAAGTAATCGAGT

TGGGAAGCCACTGCTACCGCCCAGATATGTACAACTTTGAAACCACTCTG

GTGGCCAGGTAAGAAATAAACCAAAGAGCCCTTCTGAACTGGAGCTCTTG

GTCTGATATGGCATTTTCAAGGCTGGAAAACTGCTCTATCAGACCAAACG

-continued

GATGCTGAATTTCAGGGTCTTTGGTCTGGATATGCAGCAGCGCTCCAAGG

CGTCGAGTTTCTCAAACGAGCATTGGTATCGATGACACCCTGAAAGGCCC

TTAGAAGCGATTCTGTGAGGTCGAGTTCCCAGGGTTTGAGTGCAAGTTTT

TTACGTGAA

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below. Additionally, statements made herein characterizing the invention refer to an embodiment of the invention and not necessarily all embodiments.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

The invention claimed is:

1. A method for microbial production of D-xylonate from D-xylose,
  comprising
  converting D-xylose to D-xylonate in a coryneform bacterium in which the activity of the iolR gene is reduced or completely switched off compared with the wild type or a mutant of the wild type, or the iolR gene is completely or partially deleted, wherein the wild type of the coryneform bacterium is *Corynebacterium* or *Brevibacterium*.

2. The method of claim 1,
  wherein
  the coryneform bacterium is not recombinantly modified.

3. The method of claim 1,
  wherein
  the coryneform bacterium is selected from the group consisting of *Corynebacterium* and *Brevibacterium*.

4. The method of claim 3,
  wherein
  the coryneform bacterium is selected from the group consisting of
  *Corynebacterium glutamicum* ATCC13032
  *Corynebacterium acetoglutamicum* ATCC15806
  *Corynebacterium acetoacidophilum* ATCC13870
  *Corynebacterium thermoaminogenes* FERM BP-1539
  *Brevibacterium flavum* ATCC14067
  *Brevibacterium lactofermentum* ATCC13869 and
  *Brevibacterium divaricatum* ATCC14020.

5. The method of claim 1,
  wherein
  the iolR gene is partially or completely deactivated by using myo-inositol as a substrate/inductor of iolR, by inserting a vector or another gene sequence into the gene segment of the iolR gene in which the modification affects the activity of the iolR gene, or by modifying signal structures of gene expression.

6. The method of claim 1, wherein
D-xylonate is produced on a defined, D-xylose-containing medium.

7. A modified coryneform bacterium, wherein
the activity of the iolR gene is reduced or completely switched off compared with the wild type or a mutant of the wild type or the iolR gene is completely or partially deleted, wherein the wild type of the coryneform bacterium is *Corynebacterium* or *Brevibacterium*.

8. The modified coryneform bacterium of claim 7, wherein the modified coryneform bacterium is not recombinantly modified.

9. The modified coryneform bacterium of claim 7, wherein
the modified coryneform bacterium is selected from the group consisting of *Corynebacterium* and *Brevibacterium*.

10. The modified coryneform bacterium of claim 7, wherein
the modified coryneform bacterium is selected from the group consisting of
*Corynebacterium glutamicum* ATCC13032
*Corynebacterium acetoglutamicum* ATCC15806
*Corynebacterium acetoacidophilum* ATCC13870
*Corynebacterium thermoaminogenes* FERM BP-1539
*Brevibacterium flavum* ATCC14067
*Brevibacterium lactofermentum* ATCC13869 and
*Brevibacterium divaricatum* ATCC14020.

11. The modified coryneform bacterium of claim 7, wherein
the iolR gene is partially or completely deactivated by using myo-inositol as a substrate/inductor of iolR, by inserting a vector or another sequence into the gene segment of the iolR gene, or by modifying the signal structures of gene expression.

12. The method of claim 3, wherein the coryneform bacterium is selected from the group consisting of *Corynebacterium glutamicum, Corynebacterium acetoglutamicum, Corynebacterium thermoaminogenes, Brevibacterium flavum, Brevibacterium lactofermentum* and *Brevibacterium divaricatum*.

13. The modified coryneform bacterium of claim 9, wherein the modified coryneform bacterium is selected from the group consisting of *Corynebacterium glutamicum, Corynebacterium acetoglutamicum, Corynebacterium thermoaminogenes, Brevibacterium flavum, Brevibacterium lactofermentum* and *Brevibacterium divaricatum*.

14. The method of claim 5, wherein the signal structures of gene expression include repressor genes, activator genes, operators, promoters, attenuators, ribosome bonding points, start codons, terminators, mutations in the form of transitions, transversions, insertions or deletions.

15. The method of claim 1, wherein the activity of the iolR gene is reduced or completely switched off compared with the wild type bacterium, wherein the wild type of the coryneform bacterium is *Corynebacterium* or *Brevibacterium*.

16. The modified coryneform bacterium of claim 7, wherein the activity of the iolR gene is reduced or completely switched off compared with the wild type bacterium, wherein the wild type of the coryneform bacterium is *Corynebacterium* or *Brevibacterium*.

17. The method of claim 1, wherein the activity of the iolR gene is reduced or completely switched off compared with a mutant of the wild type bacterium, wherein the wild type of the coryneform bacterium is *Corynebacterium* or *Brevibacterium*.

18. The modified coryneform bacterium of claim 7, wherein the activity of the iolR gene is reduced or completely switched off compared with a mutant of the wild type bacterium, wherein the wild type of the coryneform bacterium is *Corynebacterium* or *Brevibacterium*.

19. The method of claim 1, wherein the iolR gene is completely or partially deleted.

20. The modified coryneform bacterium of claim 7, wherein the iolR gene is completely or partially deleted.

* * * * *